(12) United States Patent
Garvin

(10) Patent No.: US 6,273,870 B1
(45) Date of Patent: Aug. 14, 2001

(54) RETRACTABLE NEEDLE AND SYRINGE COMBINATION

(75) Inventor: David M. Garvin, Coral Gables, FL (US)

(73) Assignee: Retrax Safety Systems, Inc., Miami, FL (US)

( * ) Notice: Subject to any disclaimer, the term of this patent is extended or adjusted under 35 U.S.C. 154(b) by 0 days.

(21) Appl. No.: 09/575,007

(22) Filed: May 19, 2000

(51) Int. Cl.[7] ................................................. A61M 5/00
(52) U.S. Cl. ......................... 604/110; 604/187; 604/218; 604/240
(58) Field of Search ................................... 604/195, 110, 604/187, 218, 240, 241, 243, 181, 226, 222, 221, 228, 235, 242; 222/386, 387

(56) References Cited

U.S. PATENT DOCUMENTS

| 4,973,308 | * | 11/1990 | Borras et al. ........................ 604/110 |
| 5,069,225 | * | 12/1991 | Okamura ............................. 128/765 |
| 5,092,853 |   | 3/1992  | Couvertier . |
| 5,484,421 | * | 1/1996  | Smocer ............................... 604/195 |
| 5,616,136 | * | 4/1997  | Shillington et al. ................. 604/240 |
| 5,681,292 |   | 10/1997 | Tober et al. . |
| 5,984,898 |   | 11/1999 | Garvin . |
| 6,090,077 | * | 7/2000  | Shaw .................................. 604/195 |
| 6,096,005 | * | 8/2000  | Botich et al. ....................... 604/110 |
| 6,221,055 | * | 4/2001  | Shaw et al. ......................... 604/232 |

* cited by examiner

Primary Examiner—Richard K. Seidel
Assistant Examiner—Cris Rodriguez
(74) Attorney, Agent, or Firm—McHale & Slavin

(57) ABSTRACT

A combination hypodermic syringe and needle device in which the needle is retracted inside the syringe after completion of the injection. The device requires only one hand for operation wherein increasing the pressure on the plunger initiates an automatic retraction of the needle into the syringe. In operation, a collet is expanded and a spring biased needle retractor is engaged in response to the forward movement of a plunger. The forward end of the barrel carries a wedge which forces the collet to expand upon forward movement of the collet. A vent located in the plunger allows air to escape from the interior of the plunger as the needle assembly is retracted.

12 Claims, 6 Drawing Sheets

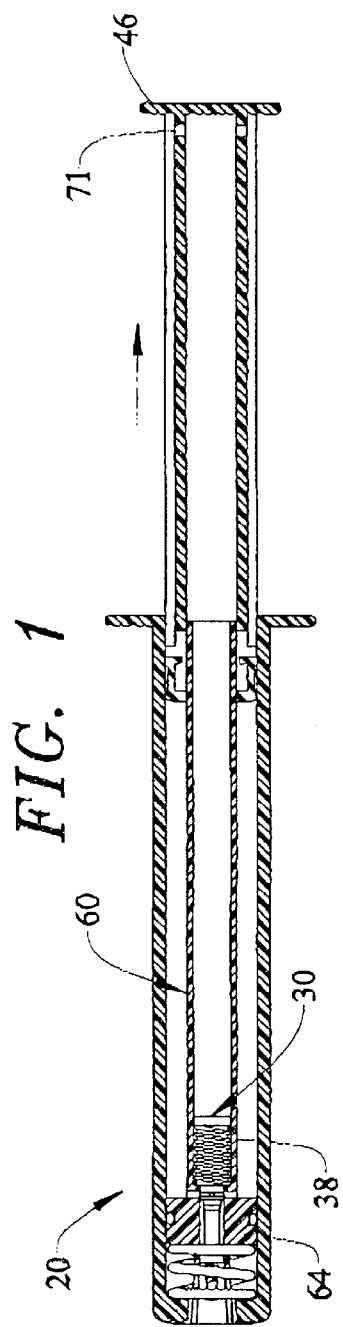
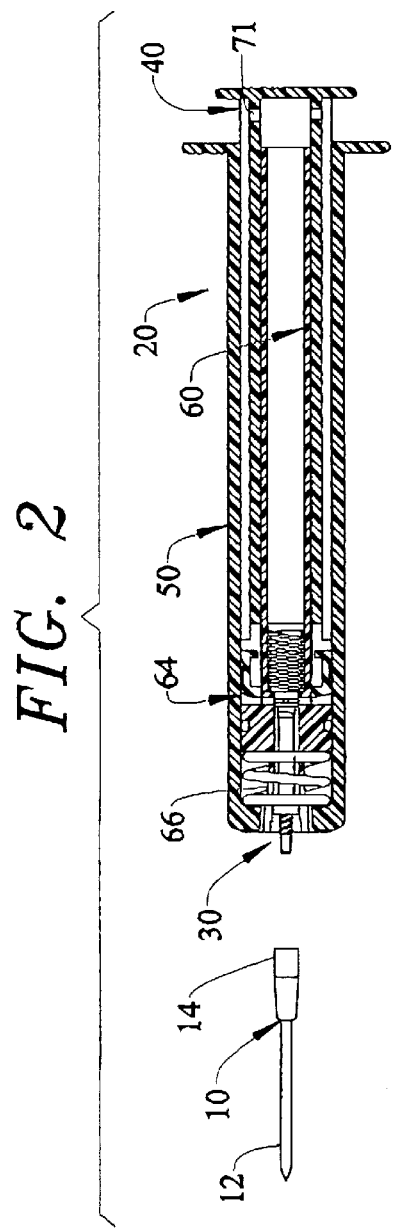
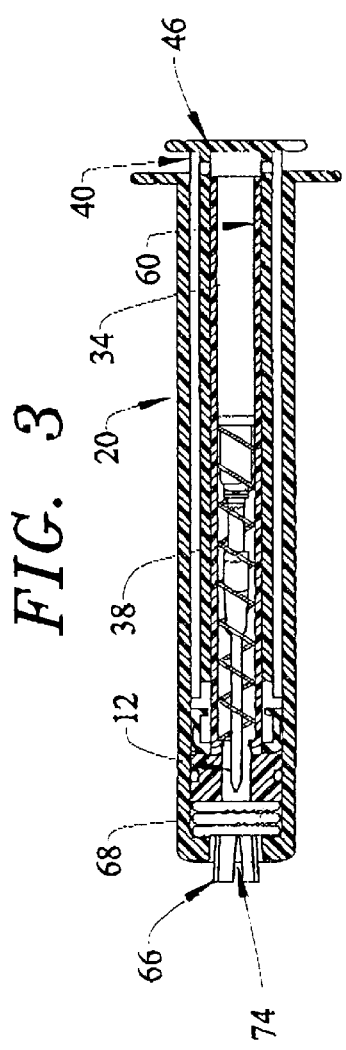

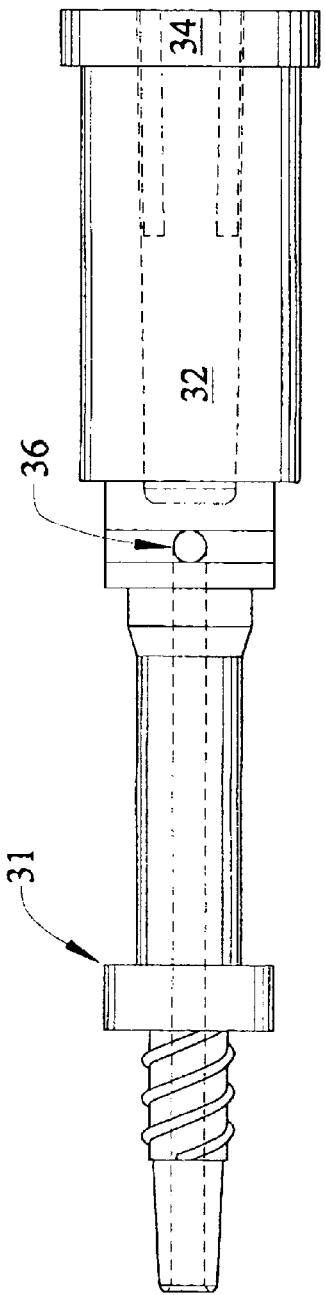
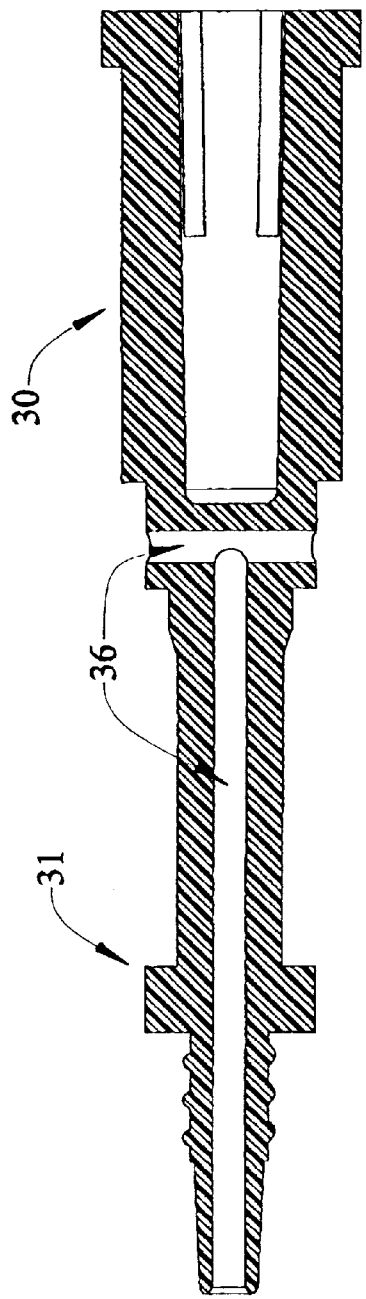
FIG. 6
FIG. 7

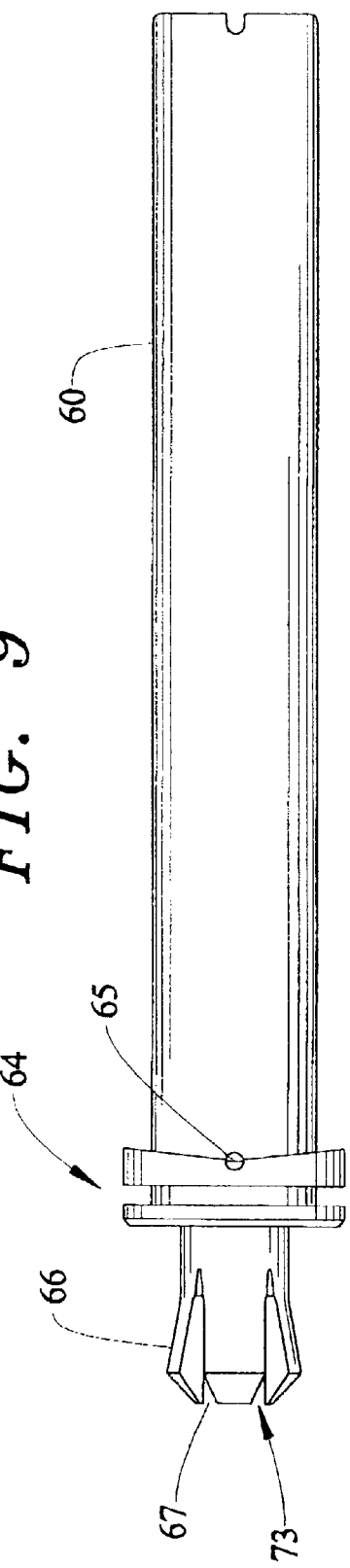
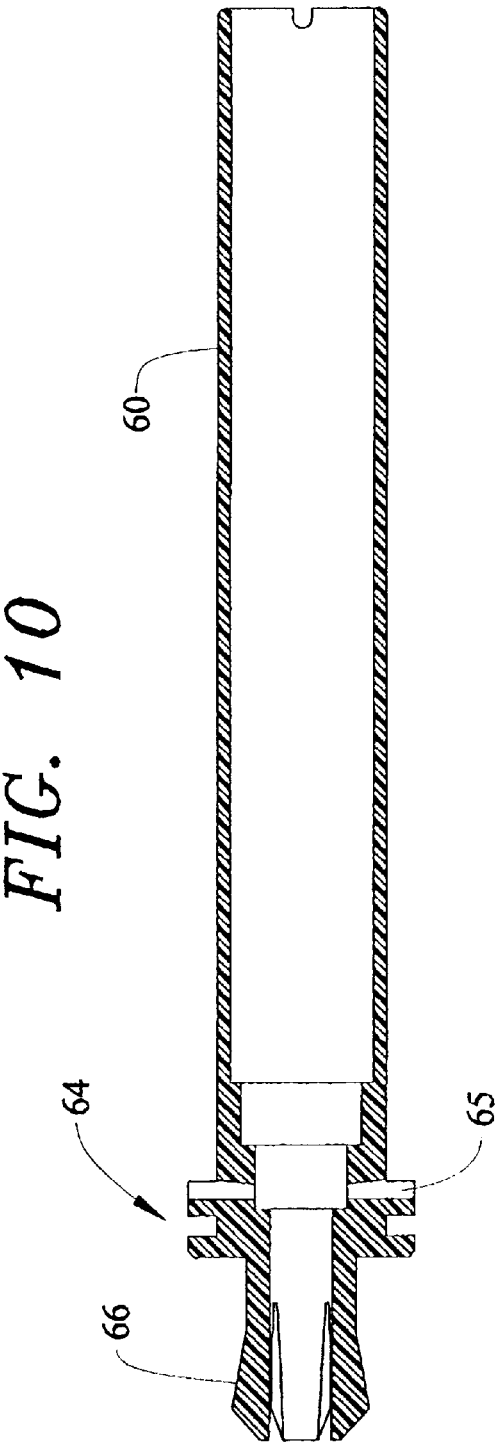

RETRACTABLE NEEDLE AND SYRINGE COMBINATION

RELATED PATENTS

This application is related to U.S. Pat. No. 5,984,898 issued Nov. 16, 1999 to Garvin and U.S. Pat. No. 5,681,292 issued Oct. 28, 1997 to Tober et al.

FIELD OF THE INVENTION

This invention relates to medical syringes including needles. More specifically, the invention relates to a combination device including a retractable needle and syringe which, following a full stroke of the syringe plunger, automatically retracts the needle into the body of the syringe thereby preventing the possibility of needle sticks.

BACKGROUND OF THE INVENTION

Many prior art hypodermic syringes have a retractable needle. The needle is manually retrieved by the forward end of the plunger after a shot has been administered. The retraction of the plunger into the barrel pulls the needle into the body of the syringe. This manipulation of the hypodermic syringe requires both hands and it is possible that the hand holding the outer barrel could come in contact with the needle before it is fully retracted.

This invention relates to hypodermic syringes which have a barrel with a needle mounted on the forward end and a plunger inserted into the rear end. After the syringe has been used, the exposed needle is contaminated and must be disposed of in such a manner as to prevent inadvertent needles sticks. This invention automatically withdraws the contaminated needle into the syringe at the completion of the plunger stroke.

DESCRIPTION OF THE PRIOR ART

Acquired Immune Deficiency Syndrome(AIDS) has increased the danger from being inadvertently stuck by a used syringe needle. It is recognized that even a minute transfer of bodily fluid from a person infected with a disease, such as AIDS, into another person's blood stream can transmit the disease. The danger is not confined to the medical community though a great majority of inadvertent needle sticks have been recorded by medical personnel. However, the increasing number of self administered drugs, both legal and illegal, pose a threat to the general population. Also, the well publicized lack of proper procedures for disposal of medical waste has also exposed the general population to contaminated needles.

Since it has been demonstrated that innocent people can be infected with such diseases as AIDS, through inadvertent needle sticks, many devices have been designed to eliminate or reduce this risk. One approach to reducing the risk involves drawing the hypodermic needle, in some manner, into the empty syringe so that the sharp end is no longer exposed. Examples of this approach are shown by U.S. Pat. No. 5,092,853, Couvertier, U.S. Pat. No. 5,681,292, to Tober, et al and U.S. Pat. No. 5,984,898 to Garvin.

SUMMARY OF THE INVENTION

An object of the present invention is to provide a hypo dermic syringe and needle that requires only one hand for operation. After the shot is completed, the same hand holding the hypodermic syringe merely increases the pressure on the plunger thereby initiating automatic retraction of the needle into the syringe.

Another object of the invention is to provide a collet which expands and releases a spring biased needle retractor in response to the forward movement of the plunger. The forward end of the outer barrel carries a wedge which insures the collet fingers will spread apart upon forward movement of the collet.

It is another object of the present invention to provide a vent in the plunger. The vent allows air to escape from the interior of the plunger as the needle assembly is retracted by or in response to spring action.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 1 is a partial sectional view of the syringe;

FIG. 2 is a partial sectional side view of a syringe shown with the plunger in the forward position, a screw mounted needle according to the present invention is also shown;

FIG. 3 is a partial sectional side view of a combination syringe and needle according to the present invention shown in the retracted position;

FIG. 6 is a planned view of the needle retractor of the present invention;

FIG. 7 is the sectional view of the needle retractor shown in FIG. 6;

FIG. 9 is a plan view of the collet;

FIG. 10 is a cross-sectional view of the collet shown in FIG. 8 along section line 9—9;

DETAILED DESCRIPTION

Figure 4:
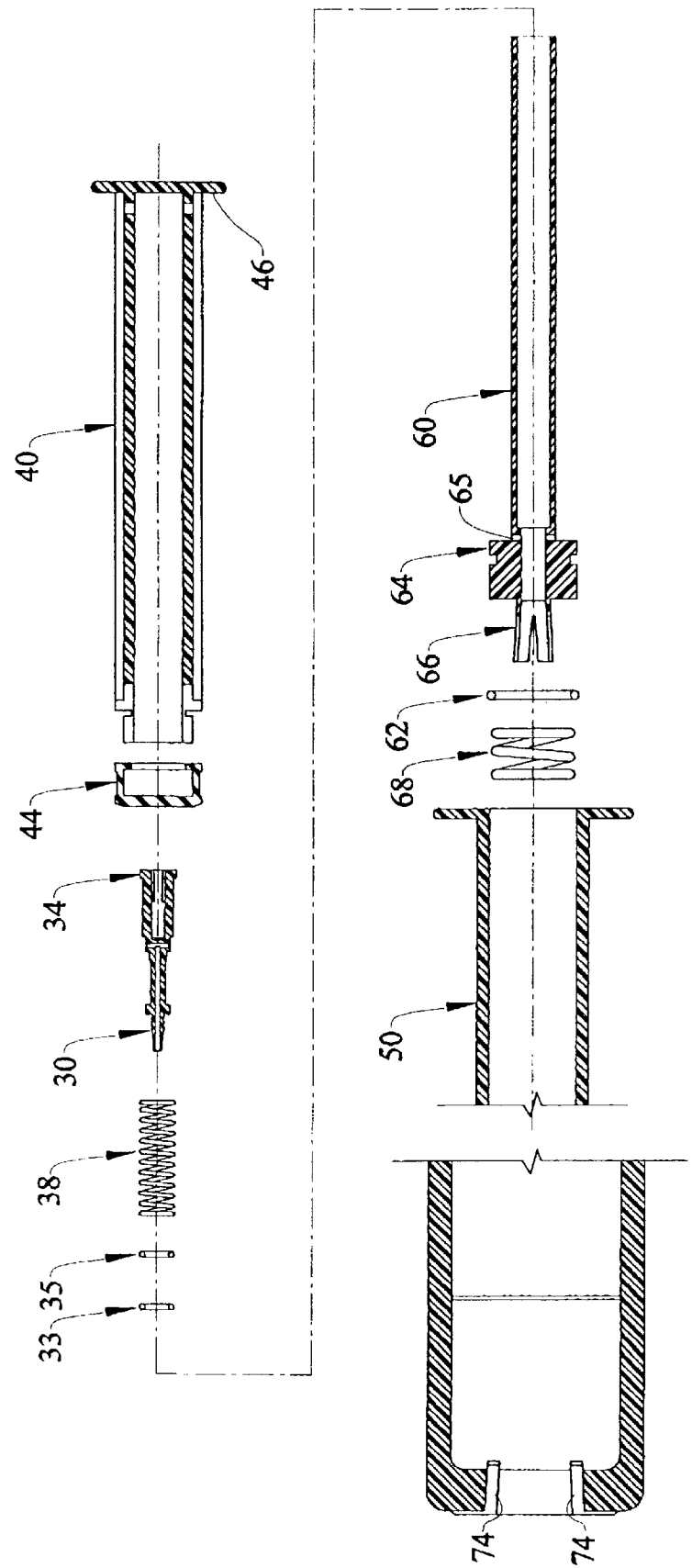
FIG. 4 is an exploded view of a syringe according to the present invention showing the assembly sequence of the component parts with the forward end of the barrel enlarged.
Figure 5:
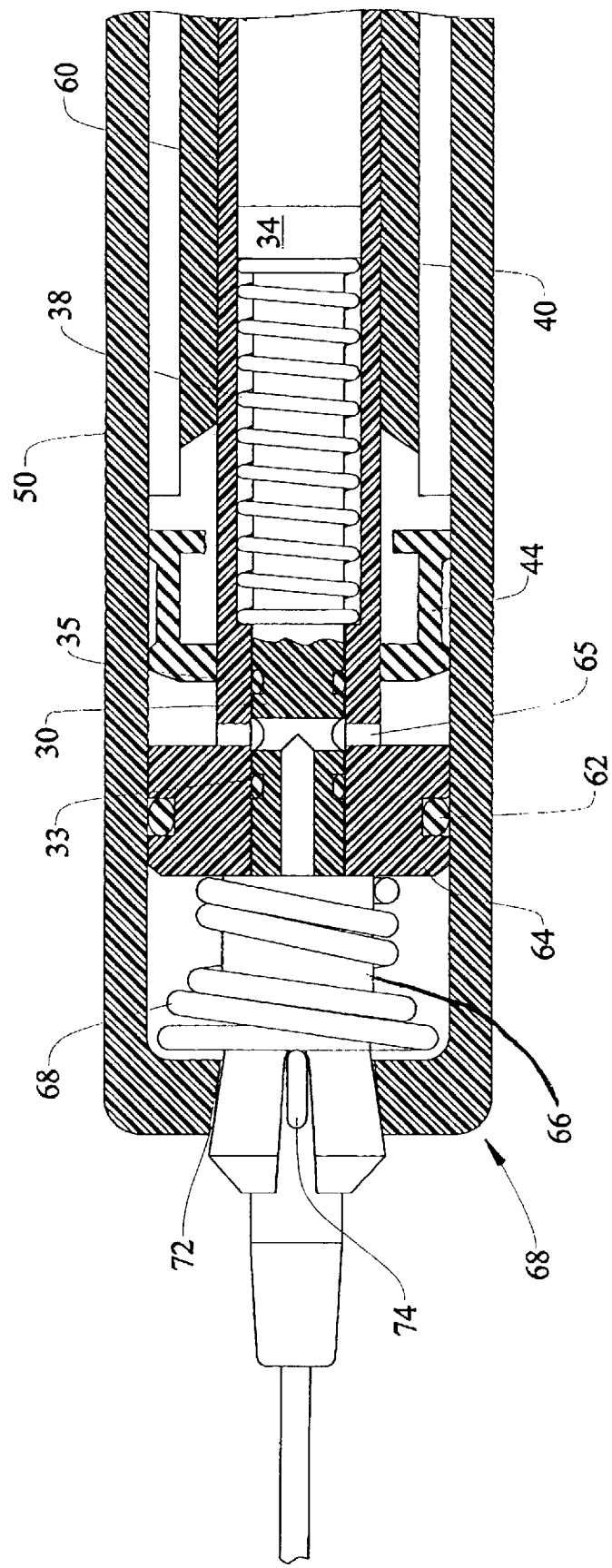
FIG. 5 is an enlarged partial sectional view of the forward end of the assemble syringe according to the present invention.

As shown in FIGS. 1–5, the invention is a combination syringe 20 and needle 10. The device features a separately attachable needle hub including a metal cannula 12 and a threaded attachment portion 14. These parts are adaptable to utilize a needle assembly which can be utilized on a conventional syringe with a female "Luer Lok" component. For smaller syringes, the needles are permanently attached to the syringe.

The syringe 20 includes a hollow inner barrel 60 which cooperates with a needle retractor 30 to draw the needle 10 into the inner barrel following use of the needle. This action is accomplished by continuing the stroke of the syringe plunger 40 following the emptying of the syringe. The continued stroke of the plunger 40 moves collet 66 forward and releases needle retractor 30 which is then propelled by spring action into the body of the inner barrel.

The syringe 20 is made up of an outer barrel or tube 50 and an inner barrel 60. The inner barrel has a forward end 64 which has an additional seal element 62, O-ring in this embodiment, which seals the inner barrel to the inner surface of the outer barrel 50. This creates a fluid containment chamber which can be pressurized by the introduction of the plunger 40 into the containment chamber from the rear end of the syringe. The plunger has a tubular body 40 and an annular plunger end 44 on a forward end of the plunger. At the rear end of the plunger a push element 46 can be provided to engage the user's thumb. A vent 71 is formed in the rear end of the plunger adjacent to push element 46. The vent 71 permits outward flow of air from the interior of the plunger when the needle 10 and retractor 30 are retracted into the plunger.

The forward end 64 of the inner barrel 60 also includes a collet 66 which includes slots 67. The collet has a slotted external funnel shape which creates a contracting and clamping effect for the collet as it is withdrawn through the opening 72 located at the forward end of the outer tube 50. The collet is biased into a clamping or retracted position by a short spring 68 which biases the inner barrel 60 rearwardly with respect to the outer tube 50.

Figure 11:
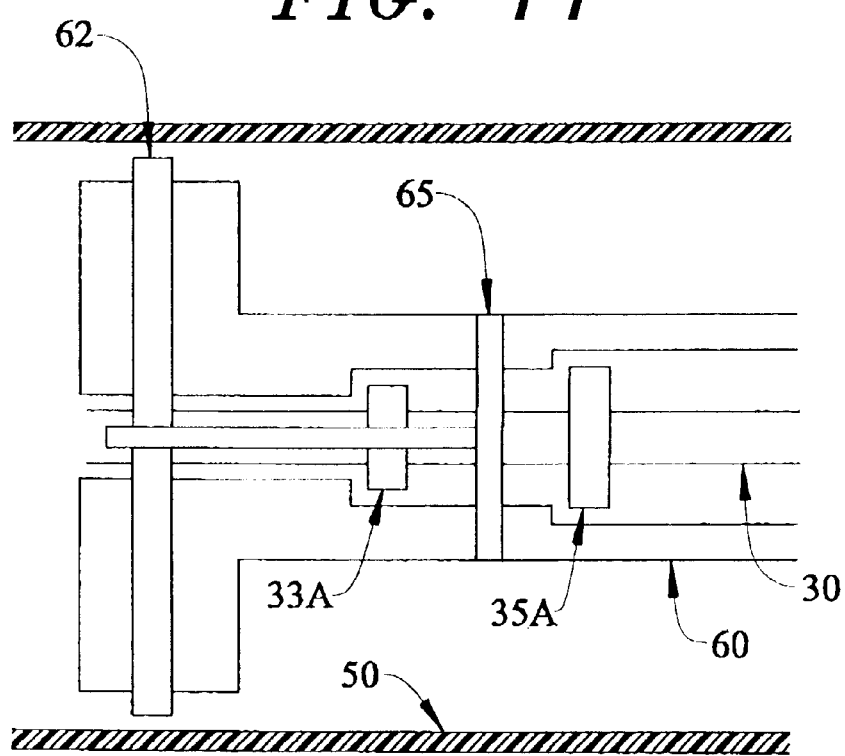
FIG. 11 shows an alternative sealed arrangement of the needle retractor wherein the O-ring type seals have been replaced with static seals.

The device further includes a retracting needle holder 30 shown in detail in FIGS. 6 and 7. The holder 30 is adapted to be inserted through the tubular body of the inner barrel 60 from a rearward end thereof. The retracting holder 30 includes a body portion 32 with an end cap 34 on the rearward end thereof and a fluid port 36 located along a mid-section of the holder and extending to the forward end thereof. The retracting holder 30 passes fluid from the containment chamber upon pressurization thereof by the plunger 40 through the fluid port 65 of the inner barrel 60 through the holder fluid port 36 into the needle 10. The holder is sealed to the inner surface of the inner barrel 60 by two seals 33 and 35. In the first embodiment shown in FIG. 17, the seals 33 and 35 are O-ring type seals. These are termed dynamic seals. An alternative embodiment of the sealing arrangement between the holder 30 and the inner barrel 60 is shown in FIG. 11 wherein static annular pressure seals 33A and 35A are used between the exterior annular edge of the holder 30 and the interior annular diameter restrictions of the inner barrel 60.

Figure 8:
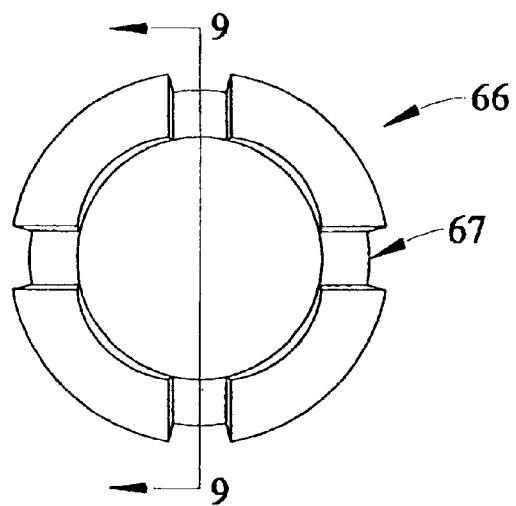
FIG. 8 is an end view of the expanding collet used in the present invention.

Details of the collet 66 of this embodiment are shown in FIGS. 8, 9 and 10. The collet includes a plurality of slots 67 which allow for expansion and contraction of the collet as the exterior funnel shape of the collet is urged forwardly and rearwardly through the forward opening 72 in outer tube 50 of the syringe 20. The slots 67 are larger at the forward ends 73 of the collet and taper rearwardly. The forward ends 73 of the slots 67 are sized to accommodate the wedges 74. When the collet 66 is urged rearwardly with respect to the outer tube 50 by a short spring 68, the slots 67 in the collet forward end are forced into a closed position, without interference from wedges 74, reducing the diameter of the collet and clamping the holder 30. This clamping and retention of the holder is helped by the trapped edge 31 which is present of the exterior of the holder 30. The collet 66 clamps onto the holder just behind the trapped edge. The trapped edge 31 is shown as an annular element in this embodiment, however, it can take on any shape which binds against the restricting edges of the collet 66 and retains the holder 30 in the forward end of the inner barrel 60.

The retracting holder 30 is biased rearwardly by long spring 38 which pushes on the end cap 34 of the holder. To release the holder 30, the collet 66 is expanded by forward movement of the collet 66 in response to contact with the inner barrel forward end 64, and the forward end 44 of the plunger. The forward movement of the collet 66 frees the collet from the constriction of the opening 72 and engages the narrowed portions 75 of the slots 67 with the wedges 74 to force the collet to expand clear of the lip on the retracting holder 30.

When a user has dispensed the fluid by a full stroke of the plunger, the plunger is pushed past the full stroke position and the plunger end 44 urges against the inner barrel 64 which in turn pushes the collet 66 forward. By pushing forward, the collet 66 expands and the holder 30 disengages from the collet 66 and the holder 30 is propelled rearwardly into the tubular body of the inner barrel 60. The syringe 20 and the needle 10 are then disabled with the needle trapped within the syringe as shown in FIG. 3.

The assembly sequence of the present invention is shown in FIG. 4 the plunger 40 and the forward end 44 are assembled. The holder 30 and the associated long spring 38 and the seals 33 and 35 are then inserted into the inner barrel 60 which is comprised of a forward end 64 and seal 62 and collet 66. The inner barrel and the short spring 68 are loaded into the outer tube 50 followed by the insertion of the assembled holder 30. The holder is inserted until engagement of the collet occurs forward followed by the insertion of the assembled plunger. The entire syringe includes four polymer plastic molded parts, namely the plunger, outer and inner barrels, the holder, and three seals, and two springs. The seals can also be a polymer and consequently be molded together with the respective inner barrel and holder as desired. By virtue of the comparatively few numbers of parts and their simplicity in execution, the present syringe and retractable needle combination can be readily and economically manufactured.

It is to be understood that while I have illustrated and described certain forms of my invention, it is not to be limited to the specific forms or arrangement of parts herein described and shown. It will be apparent to those skilled in the art that various changes may be made without departing from he scope of the invention and the invention is not to be considered limited to what is shown in the drawings and described in the specification.

What is claimed is:

1. A syringe comprising an outer barrel having a forward end and rearward end, said forward end having an opening and at least one wedge element carried in said opening, an inner barrel having a forward end and a rearward end adapted for insertion into the rearward end of said outer barrel, said inner barrel having an expandable collet mounted on said forward end thereof, spring means positioned between said outer and inner barrels so as to bias said inner barrel rearwardly with respect to said outer barrel, said collet having a forward end adapted to engage said opening in said forward end of said outer barrel, said opening constricting said collet as said collet is biased rearwardly through said opening, a fluid seal between said inner barrel and said outer barrel so as to contain fluid in a fluid containment chamber between and inner surface of said outer barrel and the exterior of said inner barrel, a needle retracting holder element having a forward end adapted to receive a needle and a shoulder trap edge, said forward end of said needle retracting holder having a diameter, said diameter of said needle retracting holder forward end being larger than a diameter of said needle, said needle retracting holder having a tubular body and a fluid port contained therein, said fluid port communicating with said fluid containment chamber and said needle, said needle retracting holder inserted into said inner barrel and engaged by said expandable collet at said shoulder trap edge, second spring means for biasing said needle retracting holder rearwardly positioned between said inner barrel and said needle retractor, and a plunger element having a forward end and a rearward end adapted for insertion into said containment chamber for pressurizing said fluid containment chamber whereby forward movement of said inner barrel with respect to said outer barrel releases said needle retractor element rearwardly into said inner barrel.

2. A syringe as in claim 1 further comprising a vent in said rearward end portion of said plunger.

3. A syringe as in claim 2 further comprising a needle connected to the forward end of said needle retractor element.

4. A syringe as in claim 3 further comprising screw attachment means for attaching said needle to a forward end of said needle retractor.

5. A syringe as in claim 2 wherein said spring means comprises a coil spring.

6. A syringe as in claim 2 wherein said second spring means comprises a coil spring.

7. A syringe as in claim 2 wherein said forward end of said inner barrel has a fluid port connecting said fluid containment chamber with said fluid port of said needle retracting holder and said forward end of said inner barrel is enlarged to form a first seal between said outer barrel portion and said inner barrel.

8. A syringe as in claim 7 wherein said first seal means comprises a separate O-ring type seal mounted on said forward end of said inner barrel.

9. A syringe as in claim 7 further comprising second and third separate seal means on said needle retracting holder for sealing said needle retracting holder to said inner barrel.

10. A syringe as in claim 9 wherein said second and third separate seal means comprise O-ring type seals.

11. A syringe as in claim 9 wherein said second and third separate seal means comprise annular static seals.

12. A syringe as in claim 2 wherein said expandable collet has a funnel shaped exterior and includes slots which enable expansion in contraction of the longitudinal passageway located within said collet.

* * * * *